(12) United States Patent
Strand et al.

(10) Patent No.: US 9,220,667 B2
(45) Date of Patent: Dec. 29, 2015

(54) STANNOUS CHLORIDE COMPOSITIONS

(75) Inventors: Ross Strand, Bracknell (GB); Owen Thurlby, Guildford (GB)

(73) Assignee: The Procter & Gamble Company, Cincinnati, OH (US)

( * ) Notice: Subject to any disclaimer, the term of this patent is extended or adjusted under 35 U.S.C. 154(b) by 1022 days.

(21) Appl. No.: 12/480,236

(22) Filed: Jun. 8, 2009

(65) Prior Publication Data

US 2010/0310614 A1   Dec. 9, 2010

(51) Int. Cl.
*A61K 8/19* (2006.01)
*A61K 8/25* (2006.01)
*A61Q 11/00* (2006.01)
*A61K 8/20* (2006.01)

(52) U.S. Cl.
CPC ... *A61K 8/25* (2013.01); *A61K 8/19* (2013.01); *A61K 8/20* (2013.01); *A61Q 11/00* (2013.01); *A61K 2800/412* (2013.01)

(58) Field of Classification Search
None
See application file for complete search history.

(56) References Cited

U.S. PATENT DOCUMENTS

| 1,597,653 | A | * | 8/1926 | Little | 205/506 |
|---|---|---|---|---|---|
| 2,970,056 | A | * | 1/1961 | Benson et al. | 424/490 |
| 4,308,252 | A | * | 12/1981 | Tomaich et al. | 424/52 |
| 5,182,046 | A |   | 1/1993 | Patton |   |
| 6,562,461 | B1 |   | 5/2003 | Clough |   |

FOREIGN PATENT DOCUMENTS

| WO | WO 93/07850 | | 4/1993 |
|---|---|---|---|
| WO | WO 9307850 A1 | * | 4/1993 |
| WO | WO 98/04234 | | 2/1998 |
| WO | WO 01/68046 | | 9/2001 |
| WO | WO 2007/074262 | | 7/2007 |
| WO | WO 2007/136381 | | 11/2007 |

OTHER PUBLICATIONS

Supersil Chemical(I) Pvt.Ltd., Different Grade of Precipitated Silica, printed from http://www.maharashtradirectory.com/catalog/supersilsilica/, with Google entry and availbility date of Apr. 26, 2005, 8 pages.*
Gitiliz et al., Encyclopedia of Chemical Technology—Tin Compounds:Stannous Chloride, Jan. 27, 2006, vol. 24, p. 1-3, 4 pages with cover sheet.*
Irani et al., Flow Conditioning and Anticaking Agents, Ind. Eng. Chem. , 1959, 51 (10), pp. 1285-1288.*
http://aerogel.nmcnetlink.com, Aerogel: Aerogel History Part I—The Father of Aerogels, 2005, printed from http://aerogel.nmcnetlink.com/aerogel-history-1.html, 2 pages.*
European Search Report, EP Application No. 08157975.7-2108, dated Jan. 27, 2009.

* cited by examiner

*Primary Examiner* — Gigi Huang
(74) *Attorney, Agent, or Firm* — Alexandra S. Anoff

(57) ABSTRACT

The invention relates to a particulate composition comprising:
 c) a particulate source of stannous chloride;
 d) and silicon dioxide (also referred to as hydrated silica or silica).

The invention further relates to a method for improving the flowability of particulate stannous chloride by admixing silica with it. The composition of the invention has been found to give improved flow properties to stannous chloride when compared to the absence of an anti-caking agent, as assessed via methods of powder characterization detailed in the European Pharmacopoeia.

3 Claims, 1 Drawing Sheet

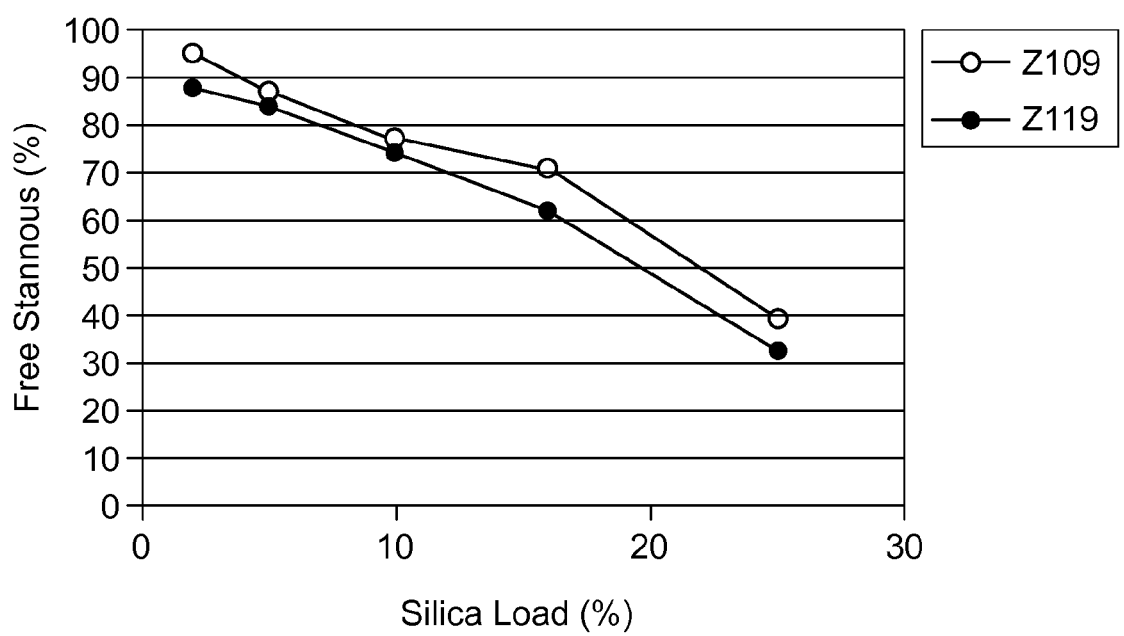

STANNOUS CHLORIDE COMPOSITIONS

FIELD OF THE INVENTION

The present invention relates to particulate oral compositions comprising a tin (II) salt and an anti-caking agent. The compositions are valuable for use in the preparation of oral compositions.

BACKGROUND OF THE INVENTION

Tin (II) (stannous) ions, provided in oral compositions by stannous chloride and/or other stannous salts, have long been valued for the multiple benefits that they can afford, including antimicrobial effects, control of breath malodor, control of dental plaque growth and metabolism, reduced gingivitis, decreased progression to periodontal disease, reductions in dentinal hypersensitivity, and reduced coronal and root dental caries and erosion.

The use of stannous chloride as a raw material can pose problems. Stannous (II) chloride, both dihydrate and anhydrous forms, are hygroscopic materials and thus attract water vapour from the air through both absorption and adsorption. This makes the powdered compound sticky. Particles can bind together, agglomerates can form during transit and storage and thus flowability during processing is difficult.

It has been a problem in the art to ship, store and handle stannous (II) ion salts due to the handling problems discussed above. Accomplishing flow of stannous ion salts from storage bins has proven to be difficult. Ideal flow design would be a simple storage bin with wall angles steep enough to promote mass flow. However, stannous chloride cakes so readily that simple mass flow design does not work. Both the Peschl Shear Tester and bin design calculations indicate that the wall angles of the bin need to be near vertical with a large outlet dimension.

The use of an anti-caking agent can improve the flow, decrease the compaction and therefore decrease restricted flow during processing. Anti-caking agents function either by adsorbing excess moisture or by coating particles to make them less prone to water adsorption. Other compounds are known to experience similar problems to stannous chloride, for example, potassium nitrate. WO 2007/136381 discloses that the addition of dipotassium hydrogen phosphate and potassium dihydrogen phosphate to potassium nitrate maintains a free flowing state.

The production of an abrasive toothpaste containing stannous has also presented compatibility problems. Although silica abrasives are widely used within toothpastes, the surface hydroxyl groups on the silica particles can deactivate stannous ions in combination with other factors, e.g. pH and water. The combination of silica with stannous ions has shown loss of bioavailability of the stannous over the shelf life of the toothpaste. The present invention discloses a composition comprising stannous chloride with silica as an anti-caking agent. For simplicity, the use of dentifrice grade silica as an anti-caking agent to improve the flow is advantageous for both manufacturing simplicity and well accepted worldwide safety and regulation profiles. It has been found that stannous chloride dihydrate can be maintained in a free flowing condition when admixed with silica dioxide with minimal loss in the activity of the stannous chloride due to the small amounts of silica utilised and the low water activity which inhibits stannous ion transfer to the silica.

SUMMARY OF THE INVENTION

The present invention relates to a particulate, solid composition comprising:
a) a particulate source of stannous chloride;
b) and silicon dioxide (also referred to as hydrated silica or silica),
and the use of the particulate composition in the manufacture of oral compositions, such as toothpastes.

The invention further relates to a method for improving the flowability of particulate stannous chloride by admixing silica with it. The composition of the invention has been found to give improved flow properties to stannous chloride when compared to the absence of an anti-caking agent, as assessed via methods of powder characterisation detailed in the European Pharmacopoeia.

BRIEF DESCRIPTION OF THE DRAWINGS

FIG. 1 is a graph of silica interactions with stannous for two different silicas.

DETAILED DESCRIPTION OF THE INVENTION

Unless specified otherwise, all percentages and ratios herein are by weight of the total particulate composition and all measurements are made at 25° C.

The present invention relates to stannous chloride raw materials and their mixture with silica to form an intermediate for use in the preparation of oral compositions such as toothpastes or gels. The essential components of the present invention are stannous chloride and silica.

Stannous Chloride

The choice of using of stannous (II) chloride as the salt to provide the oral care benefits versus other stannous salts is driven by the cost of the material, its purity and the ability to adjust the stannous loading within local country regulations. Stannous chloride is available in both dihydrate and anhydrous forms. The anhydrous grade can be supplied in various forms: powder, flake and pellets. Stannous chloride dihydrate is commercially available from various suppliers. Physical characteristics include a colorless crystalline material with a slight characteristic odor, poor flow characteristics and a relatively short shelf life. However, the disadvantages of using stannous chloride, either in the dihydrate or anhydrous form, are the manufacturing constraints, both in shipping and handling. Both the dihydrate and the different anhydrous forms, to a greater or lesser extent, are hygroscopic, making flowability during processing difficult and giving a poor activity over the shelf life of the material. Stannous chloride is also an aggressive reducing agent to some metals. This property can lead to the formation of undesirable compounds because the material cakes and sits on dead spots in storage bins.

It has now been found that stannous (II) chloride can be maintained in a free flowing condition when admixed with silica with minimal activity loss in the activity of the stannous chloride due to the small amounts of silica utilised and the low water activity which inhibits stannous ion transfer to the silica. Studies have indicated that no segregation occurs when silica is mixed with stannous chloride dihydrate at greater than 0.5% by weight silica admixed. The resulting mixture is a particulate, solid composition. Preferably silica is mixed with stannous chloride dihydrate within the range of 0.5-10%, more preferably 0.5-5% by weight silica admixed. The ratio of silica to stannous chloride is in the range from 0.5:99.5 to 10.0:90.0, preferably from 1.0:99.0 to 5.0:95.0 and more preferably from 2.0:98.0 to 3.0:97.0. The particulate, solid composition of the present invention generally comprises at least 90% stannous (II) chloride, preferably at least 95% stannous (II) chloride.

Silica is blended at low levels with either stannous chloride dihydrate or anhydrous via appropriate powder mixing, i.e. tumble mixing. The uniform blend provides a stable, free flowing material that improves the handling and shipping of the stannous chloride over the shelf life of the material compared with the commercially available stand alone stannous chloride material. Furthermore, maintaining a low ratio of silica to stannous chloride does not pose the normal deactivation seen with silica and stannous in toothpastes due both to the higher concentration of stannous to silica and the lower water availability.

Silica

Silica is utilised herein because of both its unique benefits of exceptional dental cleaning and polishing performance without unduly abrading tooth enamel or dentine and its property as an anti-caking agent. Silica abrasive polishing materials herein generally have an average particle size ranging from 0.5 to 30 μm, and preferably from 5 to 15 μm. An exemplary method to measure the particle size of the silica is to use the Malvern Mastersizer® S particle size analyzer, which yields a volume distribution of the particle size, commercially available from Malvern Instruments Ltd., Worcestershire, WR14 1XZ, UK. The instrument should be operated following Malvern standard procedures and guidelines as defined in the equipment manual. Other equivalent instruments may also be used. The abrasive can be precipitated silica or silica gels such as the silica xerogels described in U.S. Pat. Nos. 3,538,230 and 3,862,307. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the composition of the present invention are described in more detail in U.S. Pat. Nos. 4,340,583, 5,603,920, 5,589,160, 5,658,553, 5,651,958 and 6,740,311. The U.S. Pat. No. 6,740,311 describes these silicas as synthetic hydrated amorphous silicas containing about 3% to about 10% by weight of moisture, and extensively discloses their method of manufacture and physical properties. Most preferred for the present composition is Zeodent® 119 with an average particle size of 6-15 μm.

The composition of the present invention can be mixed with other ingredients detailed below to form an oral composition. Preferred oral compositions comprise one or more oral care agents selected from a source of fluoride ions, an additional dental abrasive, a flavour, a humectant, one or more chelants and mixtures thereof.

Fluoride Ions

It is common to have a water-soluble fluoride compound present in dentifrices and other oral compositions in an amount sufficient to give a fluoride ion concentration sufficient to provide anticaries effectiveness. The oral composition herein preferably comprises a fluoride ion source sufficient to provide from 0.01% to 0.35% (100 to 3500 ppm), preferably from 0.03% to 0.2% by weight of the oral composition (300 to 2000 ppm) fluoride ion. A wide variety of fluoride ion-yielding materials can be employed as sources of soluble fluoride in the present compositions. Representative fluoride ion sources include: stannous fluoride, sodium fluoride, potassium fluoride, sodium monofluorophosphate, indium fluoride and many others. Preferred sources of fluoride ion are stannous fluoride and sodium fluoride, as well as mixtures thereof.

Abrasive

Dental abrasives are useful in oral compositions such as tooth pastes and gels for their ability to remove surface stain and pellicle and for polishing the teeth. In addition to silica, further dental abrasives can be included in the oral composition. Dental abrasives useful in the oral composition include many different materials. Suitable abrasives include, for example, insoluble sodium polymetaphosphate, hydrated alumina, and resinous abrasive materials such as particulate condensation products of urea and formaldehyde. Particulate thermo-setting polymerized resins, for example, melamines, phenolics, ureas, melamine-ureas, melamine-formaldehydes, urea-formaldehyde, melamine-urea-formaldehydes, cross-linked epoxides, and cross-linked polyesters are also suitable. Mixtures of abrasives can be used.

Chelants

The oral composition of the invention may comprise one or more chelants, also known as chelating agents, having a molecular weight (MW) of less than 1000. The term "chelant", as used herein means a bi- or multidentate ligand having at least two groups capable of binding to divalent metal ions.

Water

The term "orally acceptable carrier" as used means a liquid or semi-solid vehicle such as a paste or a gel for containing the active ingredients of oral composition and delivering them to the oral cavity. Water is commonly used as a carrier material in oral compositions. It is useful as a processing aid, is benign to the mouth and it assists in quick foaming of toothpastes. Water may be added as an ingredient in its own right or it may be present as a carrier in other common raw materials such as sorbitol and sodium lauryl sulphate. The carrier can also include other conventional additives in oral care compositions such as desensitizing agents, teeth whitening agents such as peroxide sources, herbal agents, buffers, anti-staining agents, thickening materials, humectants, surfactants, a flavor system, sweetening agents, and colouring agents.

The pH of the oral composition is preferably from 4.5 to 7, more preferably from 5 to 6.5. The pH of a dentifrice composition is measured from a 3:1 aqueous slurry of the dentifrice, i.e., 3 parts water to 1 part dentifrice.

Other Ingredients

The oral composition can further comprise the usual and conventional ancillary components as more fully described hereinafter.

An optional but preferred component of the compositions herein is a humectant. The humectant serves to keep the dentifrice from hardening upon exposure to air, to give a moist feel to the mouth, and, for particular humectants, to impart a desirable sweetness of flavour. The humectant, on a pure humectant basis, generally comprises from 5% to 70%, preferably from 15% to 45%, by weight of the oral composition. Suitable humectants include edible polyhydric alcohols such as glycerin, sorbitol, xylitol, butylene glycol, polyethylene glycol, and propylene glycol, especially sorbitol and glycerin.

The compositions of the present invention will generally also include a surfactant. Useful surfactant types include anionic, nonionic, cationic and betaine surfactants. Anionic surfactants can be included to provide cleaning and foaming properties, and are typically used in an amount from 0.1% to 2.5%, preferably from 0.3% to 2.5% and most preferably from 0.5% to 2.0% by weight of the oral composition. Cationic surfactants can also be used though care needs to be taken over their compatibility with other ingredients. They would typically be used at levels similar to those of the additional anionic surfactants, as would betaine surfactants.

In preparing tooth pastes or gels, it is often necessary to add a thickening agent or binder to provide a desirable consistency of the composition, to provide desirable active release characteristics upon use, to provide shelf stability, and to provide stability of the composition, etc. Thickening agents can include carboxyvinyl polymers, carrageenan, nonionic cellulose derivatives such as hydroxyethyl cellulose (HEC), and water soluble salts of cellulose derivatives such as sodium carboxymethylcellulose (NaCMC). Natural gums such as gum karaya, xanthan gum, gum arabic, and gum tragacanth can also be used herein. Suitable thickening agent levels can range from 0.1 to 5% by weight of the oral composition and higher if necessary.

Another optional component of the oral composition is a dentinal desensitizing agent to control hypersensitivity, especially salts of potassium and strontium such as potassium nitrate.

Organic antimicrobial agents may also be employed. Included among such agents are water insoluble non-cationic antimicrobial agents such as halogenated diphenyl ethers, particularly triclosan and essential oils such as thymol. Water soluble antimicrobials include quaternary ammonium salts such as cetyl pyridinium chloride. Enzymes are another type of active that may be used in the present compositions. Inorganic antimicrobial agents can also be used. One such source is zinc ions. Preferred zinc sources are zinc chloride, zinc sulphate, zinc citrate, zinc gluconate, zinc lactate and zinc glycinate. Additional sources of stannous ions can also be incorporated. Suitable stannous sources include stannous fluoride, stannous acetate, stannous gluconate, stannous oxalate, stannous sulfate, stannous lactate and stannous tartrate.

Flavoring and sweetening agents are preferably also included in the oral composition. Suitable flavoring agents and sweetening agents are well known in the art. Suitable flavor levels in the oral compositions herein are from 0.1% to 5.0%, more preferably from 0.5% to 1.5%, by weight of the oral composition. Typically, a flavor oil will be manufactured in a separate step and will comprise multiple components, natural and/or synthetic in origin, in order to provide a balanced flavour which is acceptable to a broad range of people. Flavor components can be selected from mint, spice, fruit, citrus, herbal, medicinal, and common food flavour types (e.g. chocolate). A physiological cooling agent can also be incorporated into the flavor oil. The coolant can be any of a wide variety of materials. Included among such materials are carboxamides, menthol, acetals, ketals, diols, and mixtures thereof.

Sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. An oral composition preferably contains from 0.1% to 3% by weight of these agents, more preferably from 0.1% to 1%.

The compositions may further include usual pigments, dyes and opacifiers, such as titanium dioxide. It will be appreciated that selected components for the compositions must be chemically and physically compatible with one another.

EXAMPLES

Example 1

The following example illustrates the loss in soluble stannous availability in the presence of silica. A solution based experiment demonstrates the interaction and percent free stannous availability when mixed with different concentrations of two different types of silica; Zeodent® 109 and Zeodent® 119. Solutions containing 36% by weight glycerine (liquid) and 0.6% by weight sodium gluconate (solid) (to prevent oxidation and hydrolysis of stannous ions) were made and individually added to various amounts of silica (from ranges of zero to 25% by weight). Thus the amount of silica was the single experimental variable (see table below). The total weight was adjusted with water and then finally sodium fluoride and stannous chloride (0.243 and 0.654% by weight respectively) were added. The mixtures were allowed to mix for 24 hours and then analyzed for soluble stannous (free unbound stannous) via inductively coupled plasma after centrifugation and a 1:3 dilution with water.

TABLE 1

|  | % by weight |
|---|---|
| Glycerine | 36.00 |
| Sodium Fluoride | 0.243 |
| Stannous Chloride | 0.654 |
| Sodium Gluconate | 0.6 |
| Silica | 0-25 |
| Water | to 100 |
|  | 100 |

The graph in FIG. 1 demonstrates the significant impact of silica interaction with stannous in solution. These results provide conclusive evidence that the combination of stannous and silica can impact the therapeutic benefits of stannous availability.

Example 2

In order to determine the stannous ion stability in the solid particulate composition of the present invention, a Raw Material Stability assay was carried out which compared stannous chloride dihydrate alone with stannous chloride dihydrate mixed with 3% silica Zeodent® 119. Soluble stannous levels were measured using atomic absorption. At 25° C. and 60% relative humidity and at 40° C. and 75% relative humidity there was no significant difference between the stannous stability in the stannous-silica blend as compared with the stannous without the silica over a four week period. This compares with a drop to 85% of free stannous ions in the presence of 3% silica at 25° C. in the solution assay described in Example 1. The comparative stability of the solid particulate composition of the present invention was therefore unexpected.

TABLE 2

| Raw Material Stability assay (4 week storage) | 25° C. 60% Relative Humidity | 40° C. 75% Relative Humidity |
|---|---|---|
| $SnCl_2\ 2H_2O$ | 98.4 | 94.7 |
| $SnCl_2\ 2H_2O$-silica blend | 98.8 | 97.2 |

Example 3

To ensure the optimal material blend and to minimise the formation of lumps, the mixing of the silica with the stannous chloride should be conducted at the commencement of the manufacturing process of the raw material. This will ensure uniform blending. Specifically, following the process in which the stannous chloride (dihydrate or anhydrous) is formed, 1% hydrated silica, Z119 with a particle size of 6-15 μm, is blended via tumble mixing to form a uniform mix that is then supplied for incorporation into toothpaste production. For use in the manufacture of toothpaste, the blended material is either transferred into storage bins and discharged or used directly, as per the required dosage.

Stannous chloride both with and without silica admixed were exposed to controlled environmental conditions of 30° C. & 60% relative humidity for the period of the study and assessed both for material activity & flowability.

TABLE 3

| | Stannous Chloride dihydrate (Reference Control) | | Stannous Chloride dihydrate & Hydrated Silica Blend (99:1) | |
|---|---|---|---|---|
| Time (Days) | Assay (%) | Flow Through Orifice* | Assay (%) | Flow Through Orifice* |
| Initial | 94.7 | 4.1 | 95.5 | Pass (Good Flow) 4.1 secs |
| 3 | 96.5 | Fail (No Flow) | 94.2 | Pass (Good Flow) 4.1 secs |
| 6 | 96.7 | Fail (No Flow) | 94.5 | Pass (Good Flow) 4.1 secs |
| 8 | 96.1 | Fail (No Flow) | 95.7 | Pass (Good Flow) 5.1 secs |

*Copely Flowability Tester Model BEP according to specifications detailed in the European Pharmacopoeia 2.9.16-1.

The analytical methodology to determine the stannous chloride assay is based on the average of triplicate runs for each sample. The data indicates the stability of the material over the test period with reference to the stannous dihydrate and the blended stannous dihydrate and Z119 hydrated silica. However, although there is no difference in assay between the two samples, accounting for the method variation that is within <5% relative standard deviations, there is a significant difference in flow characteristics. The reference stannous chloride dihydrate has no flow after 3 days; whereas the blended stannous chloride dihydrate & Z119 hydrated silica has good flow over the tested period. Additionally, the blended stannous chloride dihydrate also shows no visual segregation within the range of 0.5-5% by weight silica admixed.

Example 4

The following examples further describe and demonstrate the use of the present invention within toothpaste embodiments. These examples are given solely for the purpose of illustration and are not to be construed as limitations of the present invention as many variations thereof are possible.

Toothpaste compositions are shown below with amounts of components in weight %. These compositions are made using conventional methods.

TABLE 4

| Ingredient | A | B | C |
|---|---|---|---|
| Sorbitol sol. (70%) | 40.57 | 41.63 | — |
| Glycerin | — | — | qs |
| Sodium Polyphosphate | — | — | 13.00 |
| Propylene Glycol | — | — | 7.00 |
| Polyethylene glycol 300 | — | — | 7.00 |
| Phytic acid (50% soln) | 0.800 | 0.800 | — |
| Zinc citrate | 0.533 | 0.533 | — |
| Zinc lactate dihydrate | — | — | 1.50 |
| Stannous fluoride | — | 0.45 | 0.45 |
| Stannous chloride & Silica Blend 1% | 1.17 | 0.52 | 1.397 |

TABLE 4-continued

| Ingredient | A | B | C |
|---|---|---|---|
| Na fluoride | 0.321 | 0.08 | — |
| Na gluconate | 1.064 | — | 1.40 |
| Na Phosphate tribasic. dodecahydrate | — | — | 1.10 |
| Xanthan Gum | — | — | 0.25 |
| HEC | 0.30 | 0.30 | — |
| Na CMC | 1.30 | 1.20 | 0.40 |
| Carrageenan | 0.70 | 0.70 | 0.60 |
| Silica abrasive | 14.99 | 14.99 | 25.00 |
| TiO$_2$ (Anatase) | 0.53 | 0.53 | 0.50 |
| SLS (28% soln.) | 5.00 | 5.00 | 4.30 |
| Na saccharin | 0.30 | 0.30 | 0.50 |
| Flavor | 1.10 | 1.10 | 1.00 |
| NaOH 50% | 0.95 | 0.84 | — |
| Water and minors, e.g., color soln. | qs | qs | — |
| Target pH | 5.5 | 5.5 | |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is note an admission that it is prior art with respect to any invention disclosed or claimed herein or ha it alone, or in any combination with any other reference or references, teaches suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A particulate, solid composition consisting essentially of a blend of:
   a) stannous chloride dihydrate; and
   b) synthetic hydrated amorphous silica containing about 3% to about 10% by weight of water and having a particle size between about 0.5 to about 30 microns, wherein said composition contains at least 90% by weight of stannous chloride dihydrate and wherein the weight ratio of said hydrated silica to stannous chloride dihydrate is in the range from about 0.5:99.5 to about 10.0:90.0 and wherein said blend is uniform, stable and free flowing, enabling ease of shipping and handling for manufacturing of oral care compositions.

2. A composition according to claim 1 wherein said hydrated silica has a particle size between about 5 to about 15 microns.

3. A composition according to claim 1 wherein the weight ratio of said hydrated silica to stannous chloride dihydrate is about 1.0:99.0.

* * * * *